United States Patent [19]

Hinkamp

[11] Patent Number: 4,469,608

[45] Date of Patent: Sep. 4, 1984

[54] SURFACTANT COMPOSITION CONTAINING ALKYLATED BIPHENYLYL PHENYL ETHER SULFONATES

[75] Inventor: Paul E. Hinkamp, Midland, Mich.

[73] Assignee: The Dow Chemical Company, Midland, Mich.

[21] Appl. No.: 403,826

[22] Filed: Jul. 30, 1982

Related U.S. Application Data

[62] Division of Ser. No. 910,241, May 30, 1978, Pat. No. 4,357,281.

[51] Int. Cl.$^3$ .................................. E21B 43/22
[52] U.S. Cl. .......................... 252/8.55 D; 166/275; 252/353
[58] Field of Search ............... 260/512 C, 505 C; 252/8.55 D, 353

[56] References Cited

U.S. PATENT DOCUMENTS

| Re. 22,548 | 9/1944 | Brandt | 260/505 |
| 3,469,630 | 9/1969 | Hurd et al. | 252/8.55 X |
| 3,508,612 | 4/1970 | Reisberg et al. | 252/8.55 X |
| 3,811,507 | 5/1974 | Flournoy et al. | 166/274 |
| 3,945,437 | 3/1976 | Chiu et al. | 252/8.55 X |

OTHER PUBLICATIONS

Akhmedov et al., Chem. Abstract, 59, 15203h, (1960).

Primary Examiner—Herbert B. Guynn

[57] ABSTRACT

The title compounds are of the formula

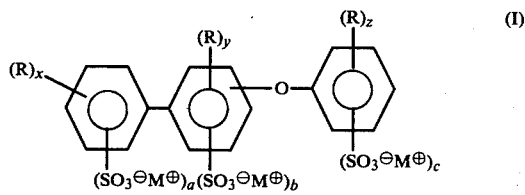

wherein
R is an alkyl radical of at least 6 carbon atoms and each R can be the same or different;
$M^{\oplus}$ is hydrogen, alkali metal ion, alkaline earth metal ion or ammonium ion radical and each $M^{\oplus}$ can be the same or different;
a, b and c are individually integers of 0 or 1 with the proviso that the $\Sigma(a+b+c)$ is equal to 2 or 3; and
x, y and z are individually integers of 0–2 with the proviso that $\Sigma(x+y+z) \geq 1$.

These compounds demonstrate good tolerance to multivalent cations, such as the cations of calcium and magnesium, good resistance to hydrolysis and are useful surfactants in enhanced oil recovery processes.

8 Claims, No Drawings

SURFACTANT COMPOSITION CONTAINING ALKYLATED BIPHENYLYL PHENYL ETHER SULFONATES

CROSS-REFERENCE TO RELATED APPLICATION

This is a divisional of application Ser. No. 910,241, filed May 30, 1978, now U.S. Pat. No. 4,357,281.

BACKGROUND OF THE INVENTION

1. Field of the Invention

This invention relates to alkylated biphenylyl phenyl ether sulfonates (A-BIPPE-S) and their use in enhanced oil recovery processes.

2. Background of the Invention

Most of the oil held in subterranean, porous rock reservoirs is produced, i.e., raised to the surface, either through the action of dissolved gases which force the oil to the surface as a froth or through a pumping action when natural reservoir pressure has been dissipated. These two production methods are termed primary oil recovery. However, such production methods usually recover less than about 25 percent of the known reservoir oil content.

Early in the 1900's, forcing water down selected well bores or injection wells to force oil through the reservoir pores to designated producing wells was accomplished successfully in Pennsylvania. Water flooding, or secondary oil recovery, has now been widely applied and presently accounts for more than half of the oil produced in the United States. This method usually adds about 15 percent to the total oil recovery from a given reservoir before the ratio of water:oil produced becomes so high (about 30:1) that the wells can no longer be operated economically.

Other methods used to recover the remaining portion (50-60 percent) of the original oil content of a reservoir are generally termed tertiary oil recovery or enhanced oil recovery methods. A variety of such methods are known and include steam flooding, miscible flooding with carbon dioxide, in situ combustion of part of the reservoir oil content, and flooding with micellar or aqueous surfactant solutions.

With regards to surfactant flooding, aqueous anionic surfactant systems are known to be useful for displacing oil from porous, subterranean rock reservoirs. These surfactant systems are generally comprised of petroleum sulfonates, often in combination with such materials as electrolytes, water-thickeners, and emulsion modifiers. While these systems demonstrate generally good efficiency, their utility is often limited by their low tolerance to multivalent cations. These cations, such as calcium and magnesium, are often encountered in brines of subterranean reservoirs and tend to form anionic surfactant precipitates or cause surfactant phase separations when contacted with aqueous anionic surfactant systems. Although the use of various cosurfactants, such as alkoxy-alcohol sulfates and aromatic ether polysulfonates, are known to improve the multivalent cation tolerance of these aqueous anionic surfactant systems, there continues a search for new such cosurfactants. Aqueous anionic surfactant systems, their tolerance problems to multivalent cations, and suggested cosurfactants for overcoming these tolerance problems are further described in U.S. Pat. No. 3,945,437, incorporated herein by reference, and the references cited therein.

SUMMARY OF THE INVENTION

According to this invention, the tolerance to multivalent cations of aqueous anionic surfactant systems useful for displacing oil from a porous, subterranean rock reservoir is improved by using as a cosurfactant an A-BIPPE-S of the formula

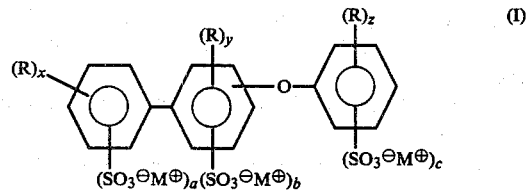 (I)

wherein

R is an alkyl radical of at least 6 carbon atoms and each R can be the same or different;

$M^\oplus$ is hydrogen, alkali metal ion, alkaline earth metal ion or ammonium ion radical and each $M^\oplus$ can be the same or different;

a, b and c are individually integers of 0 or 1 with the proviso that the $\Sigma(a+b+c)$ is equal to 2 or 3; and x, y and z are individually integers of 0–2 with the proviso that $\Sigma(x+y+z) \geq 1$.

The phenoxide radical,

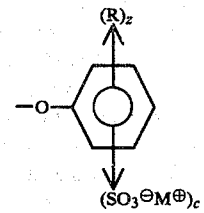

and the first phenyl radical,

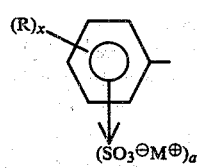

can be ortho, meta or para to one another.

The ammonium ion radicals here used are of the formula $(R')_3NH^\oplus$ (II)

wherein R' is a hydrogen, $C_1$–$C_4$ alkyl or $C_1$–$C_4$ hydroxyalkyl radical and each R' can be the same or different. Illustrative $C_1$–$C_4$ alkyl and hydroxyalkyl radicals include: methyl, ethyl, propyl, isopropyl, butyl, hydroxymethyl, hydroxyethyl, etc. Typical ammonium ion radicals include: ammonium ($N^\oplus H_4$), methylammonium ($CH_3N^\oplus H_3$), ethylammonium ($C_2H_5N^\oplus H_3$), dimethylammonium (($CH_3)_2N^\oplus H_2$), methylethylammonium ($CH_3N^\oplus H_2C_2H_5$), trimethylammonium (($CH_3)_3N^\oplus H$), dimethylbutylammonium (($CH_3)_2N^\oplus HC_4H_9$), hydroxyethylammonium ($HOCH_2CH_2N^\oplus H_3$), methylhydroxyethylammonium ($CH_3N^\oplus H_2CH_2CH_2OH$), etc. $M^\oplus$ is preferably an alkali metal ion and more preferably an ion of sodium or potassium. R is preferably an alkyl radical of between 8 and about 18 carbon atoms, and more preferably of between about 10 and about 18 carbon atoms. The alkyl radicals of R can be linear, branched or cyclic but the linear and branched radicals are preferred. The $\Sigma(x+y+z)$ is preferably equal to 1 or 2. Alkylated biphenylyl phenyl ether sulfonates wherein R is a linear or branched alkyl radical of between about 12 and about 18 carbon atoms, $M^{\oplus}$ is a sodium or potassium ion, and $\Sigma(x+y+z)$ is 1 or 2, are more preferred.

The term "sulfonate" here includes both alkylated biphenylyl phenyl ether sulfonic acids and the alkali metal, alkaline earth metal and ammonium salts thereof.

DETAILED DESCRIPTION OF THE INVENTION

A-BIPPE-A Preparation

A-BIPPE-S is prepared generally by first alkylating biphenylyl phenyl ether (BIPPE), second sulfonating the resulting alkylated biphenylyl phenyl ether (A-BIPPE), and third and optionally, converting the resulting alkylated biphenylyl phenyl ether trisulfonic acid to a corresponding alkali metal, alkaline earth metal or ammonium salt. The alkylation of BIPPE can be accomplished by any one of a number of different known methods, e.g., by reacting an unsaturated aliphatic hydrocarbon or a saturated aliphatic monohalohydrocarbon with BIPPE in the presence of a Friedel-Crafts catalyst. Of course, the aliphatic hydrocarbons correspond to the definition of R in I. A-BIPPE is preferably prepared by reacting either branched polypropylenes, such as tripropylene, tetrapropylene or pentapropylene, or a linear α-olefin, such as 1-octene, 1-decene, 1-octadecene, etc., with BIPPE in the presence of a Friedel-Crafts catalyst, such as anhydrous aluminum chloride, and at temperatures between about 40° C. and about 100° C. Polypropylene fractions consisting principally of tripropylenes ($C_9H_{18}$), tetrapropylenes ($C_{12}H_{24}$) or pentapropylenes ($C_{15}H_{30}$) are known. In general, the tripropylene fraction has a boiling range between 120° C. and 165° C.; the tetrapropylene fraction has a boiling range between 185° C. and 210° C.; and the pentapropylene fraction has a boiling range between 250° C. and 300° C. Such polypropylene fractions contain tripropylenes, tetrapropylenes and pentapropylenes, respectively, as the major or principal component. The number of alkyl substituents per BIPPE molecule can be controlled by the relative proportions of the alkylating agent and BIPPE employed in the alkylation reaction.

The sulfonation of the resulting A-BIPPE can also be accomplished by any number of known methods, e.g., by reacting the A-BIPPE with chlorosulfonic acid or sulfur trioxide in sulfuric acid. However, these known methods generally do not yield substantial amounts of di- and trisulfonated A-BIPPE, in other words, produce substantial amounts of A-BIPPE-monosulfonate and tarry by-products. As a consequence, a preferred method of sulfonating A-BIPPE is to contact the A-BIPPE

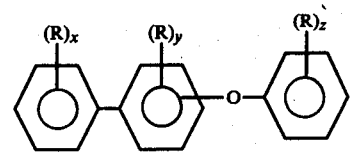

where R, x, y and z are as previously defined, with sulfur trioxide ($SO_3$) dissolved in liquid sulfur dioxide ($SO_2$). A temperature between about −10° C. and about −40° C. at 1 atmosphere is necessary to dissolve $SO_3$ in $SO_2$. At temperatures below −40° C., $SO_3$ tends to crystallize. The contacting is generally conducted in refluxing sulfur dioxide (about −10° C.). The number of sulfonate groups per molecule of A-BIPPE can be controlled by the relative proportions of the sulfonating agent and the A-BIPPE employed in the sulfonation reaction (typically at least about 3 moles of sulfur trioxide per mole of alkylated biphenylyl phenyl ether are used). This preferred sulfonating method generally yields substantially complete di- and trisulfonation (predominantly tri-) of the A-BIPPE with a minimum amount of tar formation.

Conversion of the resulting A-BIPPE-sulfonic acid is generally accomplished by first removing (typically by evaporation) any excess sulfur dioxide solvent from the crude sulfonation product. The A-BIPPE-sulfonic acid is then mixed with water and a neutralizing solution, such as a solution of sodium or potassium hydroxide, in an amount sufficient to form an aqueous solution or slurry with a pH value between about 7 and 8, containing generally between about 15-30 weight percent solids. The neutralizing solution is a solution comprising the hydroxide of $M^{\oplus}$ ions, i.e., a hydroxide solution (or oxide slurry from which the hydroxide solution can be generated in situ) of alkali metal ions, alkaline earth metal ions and/or ammonium ion radicals. The aqueous solution may be used without further treatmwent or can be dried by evaporating the water in usual ways, e.g., by spray drying or by drying on heated rolls, to recover the A-BIPPE-S in flake, granular or powdered form. The product is usually a dark, free-flowing, hygroscopic powder containing from about 90 to about 95 percent by weight of the A-BIPPE-S in admixture with small amounts of neutralized sulfate, e.g., alkali sulfate, and water.

A-BIPPE-S is soluble in water and in aqueous solutions of acids, bases or salts. For example, the preferred A-BIPPE-S (e.g., wherein R is a branched tetrapropylene or a linear α-olefin, $M^{\oplus}$ is an ion radical of sodium or potassium, and $\Sigma(x+y+z)=1$) can be dissolved in an aqueous solution containing 50 percent by weight of sodium hydroxide to form clear solutions containing 0.05 g of said product in about 15 g of the solution. These materials are surface-active agents and exhibit surface-active properties in aqueous solutions of strong electrolytes, such as acids, bases and salts. They are also useful as wetting agents, emulsifying agents or detergents.

The A-BIPPE-S of this invention can be used either singly or in combination with one another to form useful A-BIPPE-S surfactant compositions. As here used, "A-BIPPE-S surfactant composition" means a composition wherein at least about 90 weight percent of the alkylated biphenylyl phenyl ether radicals are di- and/or trisulfonated. The remaining 0-10 weight percent can comprise A-BIPPE-monosulfonates. An example of an A-BIPPE-S surfactant composition comprising a single sulfonate is a surfactant composition comprising a monoalkylated biphenylyl phenyl ether trisulfonate. An example of such a composition comprising a blend of different sulfonates is a surfactant composition comprising a 40:60 mixture of monoalkylated-BIPPE-di-:-trisulfonates. Another example of such a composition is a surfactant composition comprising an 80:20 mixture of mono-:dialkylated-BIPPE-disulfonates. Still another example of such a composition is a 50:50 blend of a 40:60 mixture of monoalkylated-BIPPE-di-:-trisulfonates and an 80:20 mixture of mono-:dialkylated-BIPPE-disulfonates. Other examples are well within the skill of an ordinary artisan. These A-BIPPE-S surfactant compositions can be used alone or in combination with other surfactant compositions, such as those comprising alkoxy-alcohol sulfates or aromatic ether polysulfonates.

A-BIPPE-S as Cosurfactants in Aqueous Anionic Surfactant Systems

The process for displacing oil from a porous, subterranean rock reservoir, the process comprising injecting into the reservoir an aqueous anionic surfactant system, is improved by injecting an aqueous anionic surfactant system that contains a sufficient amount of A-BIPPE-S to improve the system's multivalent cation tolerance without significantly reducing the interfacial tension-lowering activity of the system.

The A-BIPPE-S or surfactant compositions thereof are here used in the same manner as known cosurfactants, such as alkoxy-alcohol sulfates and aromatic ether polysulfonates. Sufficient A-BIPPE-S is dissolved in an active aqueous anionic surfactant system such that the multivalent cation and total salt tolerance of the system is increased without significantly adversely affecting the oil-displacing capability of the system. These systems containing A-BIPPE-S demonstrate improved resistance to hydrolysis and have less tendency to form viscous or stable emulsions with the oil to be displaced.

The active aqueous anionic surfactant systems suitable for use in the practice of this invention and the manner of their use for displacing oil from a porous, subterranean rock reservoir are adequately disclosed within U.S. Pat. No. 3,945,437. As disclosed therein, such systems preferentially comprise mixtures of relatively water-soluble and water-insoluble alkali metal salts of petroleum sulfonates and can be used with or without such materials as electrolytes, thickeners and the like. These other materials and their use with active aqueous anionic surfactant systems are also described within U.S. Pat. No. 3,945,437.

"Active aqueous anionic surfactant system" as here used has the same meaning as its use in U.S. Pat. No. 3,945,437, i.e., a system in which the interfacial tension between it and the oil to be displaced is less than about 0.1 dyne per centimeter.

The following examples are illustrative embodiments of this invention. Unless indicated to the contrary, all parts and percentages are by weight.

SPECIFIC EMBODIMENTS

Example 1: Alkylation of BIPPE

Powdered anhydrous aluminum chloride (4.5 g) was added to stirred, melted (approx. 60° C.) BIPPE (302 g, 1.226 mole). Within 15 minutes the aluminum chloride was dissolved producing a dark red mixture. 1-Decene (103 g, 0.736 mole) was then added in a slow stream with stirring so as to maintain a reaction temperature between about 60° C. and 90° C. After all the 1-decene had been added, the reaction was held at 80°–90° C. for about 1 hour with stirring. Subsequently, water (5 ml) was added with vigorous stirring until the dark red color of the reaction mixture disappeared. The solid aluminum oxide and reaction salts were allowed to settle, BIPPE alkylate and excess BIPPE were decanted and finally filtered while still hot (>75° C.) to yield a fairly clear, light-yellow oily mixture for distillation. Excess BIPPE was removed under vacuum (boiling range of about 147°–168° C. at 0.5 mm Hg) followed by BIPPE monoalkylate (boiling range of about 190°–265° C. at 0.5 mm Hg) leaving a tarry residue which was discarded. The following yields were obtained:

| | |
|---|---|
| BIPPE monoalkylate | 174 g |
| Residue | 22.2 g |

Example 2

Example 1 was repeated except that 1-octadecene (244 g, 0.97 mole) was substituted for 1-decene and the amounts of BIPPE and aluminum chloride were increased to 400 g and 8 g, respectively. BIPPE monoalkylate (274.7 g) was recovered over a temperature range of about 270°–312° C. at 0.5 mm Hg, the remainder being residue (132.6 g).

Example 3

Example 1 was again repeated except that tetrapropylene was substituted for 1-decene. BIPPE monoalkylate was recovered.

Example 4: Sulfonation of BIPPE Alkylates

The monoalkylate (31.2 g) of Example 1 was dissolved in about 2–3 times its volume of refluxing sulfur dioxide (approx. −10° C.). Sulfur trioxide (20.8 g) in liquid sulfur dioxide (40 ml) was subsequently slowly added at −10° C. with stirring while maintaining reflux. At the end of this time, the reaction mixture was poured into a one-liter beaker and the sulfur dioxide was allowed to evaporate under a hood. Evaporation was completed on a steam bath leaving a dark, viscous, sticky liquid which was the acid form of the mono-, di- and trisulfonated alkylates, predominantly trisulfonated.

Examples 5–6

The procedure of Example 4 was repeated substituting the monoalkylates of Examples 2 and 3, respectively, for the monoalkylate of Example 1. Similar results were obtained.

Example 7: Conversion of A-BIPPE-Di- and Trisulfonic Acids to the Corresponding Sodium Salts Water (52 g) was added to the product of Example 4 with stirring to yield a thick, dark liquid. While monitoring the pH, caustic (50 percent sodium hydroxide) was added with stirring to this liquid until a neutral pH was obtained. At this neutral point, a dramatic decrease in viscosity and some loss of color intensity was observed. Analysis of the resulting product showed:

| | |
|---|---|
| Solids | 52 percent |
| Monosulfonates | not detected |

| -continued | |
|---|---|
| Di- and trisulfonates | 100 percent |
| Sulfates | 3.75 percent |

Similar results were obtained when this example was repeated with the product of Example 5.

Liquid Chromatography Sample Identification

A 3 microliter sample of aqueous surfactants containing about 20 percent active sodium salt is injected into a stream of solvent (0.04M lithium chloride and 7.9 percent by volume n-butanol, 12.4 volume percent isopropanol and 77.7 percent water) passing through a liquid chromatographic column (5 mm diameter by 108 mm length and packed with Vydac ® AX anion exchange resin). The stream is pumped through the column and auxiliary equipment with a Miltron Roy instrument minipump at a rate of about 80 ml per hour and 120–140 psi of pressure. Mono-, di- and trisulfonates are absorbed on the column. A monosulfonate is eventually eluted from the column by the 0.04M lithium chloride solution and its presence is detected by a differential ultraviolet detector set at 254 micrometers and 0.64 optical density which compares pure solvent to the eluted stream. A signal from the detector is recorded on a standard 10 millivolt recorder. After the monosulfonate is eluted from the column (about 60 ml of solvent) the ionic strength of the solvent is increased to 0.24M lithium chloride and pumping is continued until the disulfonate is eluted from the column (about 120–150 ml of solvent). The presence of the disulfonate is detected in a manner similar to the detection of the monosulfonate. Subsequently, a second, separate response is detected as a 0.24M lithium chloride solution removes the trisulfonated product from the column. Integration of the peak areas is used for quantititative determinations.

As an example of the sulfonate distribution obtained from the practice of this invention, the product of Example 6 was determined to be:

| A—BIPPE—monosulfonate | 0% |
|---|---|
| A—BIPPE—disulfonate | 34.5% |
| A—BIPPE—trisulfonate | 65.5% |

The degree of sulfonation was thus:
0(1)+2(0.345)+3(0.655)=2.65
where 3.0 is 100 percent trisulfonation. The sample contained 45.11 percent solids and was also analyzed to contain 5.9 percent sodium sulfate.

Examples 8 and 9: A-BIPPE-S Cosurfactants in Aqueous Anionic Surfactant Systems Combinations of surfactants are used in many surfactant floods because of a property enhancement or for economic reasons. For example, Witco TRS-18 is a relatively inexpensive petroleum sulfonate which in itself is not useful for surfactant flooding, especially in the presence of brines, because of its poor solubility in water. Its equivalent weight of 495 is above the range generally conceded as useful with enhanced or recovery floods (and equivalent weight of about 400 is the generally conceded maximum). Although Witco TRS-18 is inadequately soluble in water at a 3.1 percent active level and thus separates to form two distinct phases, Witco TRS-18 in combination with the surfactants of this invention (at the same total surfactant level) form a surfactant solution with a useful degree of brine tolerance and a solution which exhibits interfacial tension values with some brine concentrations which are low enough to form an oil bank (or to spontaneously emulsify the oil present).

Tabulated below are the low interfacial tensions and the solubility demonstrated by combinations of Witco TRS-18 with a monoalkylated (propylene tetramer) 35:65 mixture of BIPPE-di-:-trisulfonates and neutralized to the sodium salt. In each example, the total surfactant concentration was held at a 3.1 percent active level, with the surfactant based on BIPPE comprising a portion of the total surfactant such that the equivalent weight of the mixture (Witco TRS-18 and A-BIPPE-S) was 430 in Example 8 and 440 in Example 9. With Witco TRS-18 alone, phase separation was complete in all examples at 70° C. and thus no interfacial tension measurements were made. All single phase samples were tested (even though cloudy) for interfacial tension at 70° C. with Soltrol ® 130 (a $C_{10}$–$C_{12}$ isoparaffin from Phillips Petroleum) as the oil phase, adopted as a compromise representation of a reservoir crude oil.

Determination of interfacial tensions between the surfactant solutions and the oil phase were made using a spinning drop technique (Cayias et al., *ACS Symposium Services No. 8*, "Adsorption at Interfaces", Amer. Chem. Soc. 1975). In this technique, a 0.5 microliter droplet of oil is placed in a test tube of 2 mm I.D. and 4 inches of length filled with surfactant. The test tube is then rotated on its major axis horizontally at high speeds (5,000 to 10,000 rpm or 6 to 12 msec/rev). Under these conditions, the less dense phase (oil) assumes a central position as the more dense phase is forced outward. The droplet shape in the center tends to appear long and narrow in shape if the interfacial tension forces are not strong enough to maintain sphericity. The diameter of this cylindrical drop, the difference in phase density and the rotational speed can then be used to calculate the interfacial tension if the length to diameter ratio is greater than 4:1 using the relatively simple formula $$\gamma = K(d_2 - d_1)\frac{dia^3}{P^2}$$

where
$\gamma$ = interfacial tension, dynes/cm
K = 522,032
$d_2$ = density of more dense phase
$d_1$ = density of less dense phase
dia = diameter of the droplet
P = rotational speed in msec/rev A low interfacial tension value (less than 0.1 dyne/cm) is generally conceded to be necessary in order for a surfactant solution to displace oil and thus form an oil bank in an oil reservoir subject to tertiary oil recovery techniques.

| INTERFACIAL TENSIONS OF VARIOUS COMBINATIONS OF WITCO TRS-18 AND A—BIPPE—S | | | |
|---|---|---|---|
| Ex. | NaCl (N)[1] | Appearance | Interfacial Tension (dynes) |
| 8 | 0.1 | Cloudy | 0.026 |
|  | 0.2 | " | 0.0075 |
|  | 0.3 | " | 0.0022 |
|  | 0.4 | " | 0.0013 |
|  | 0.5 | " | 0.0016 |
|  | 0.6 | " | 0.0013 |
|  | 0.7 | Two Phases | S.E.[2] |

| | INTERFACIAL TENSIONS OF VARIOUS COMBINATIONS OF WITCO TRS-18 AND A—BIPPE—S | | |
|---|---|---|---|
| Ex. | NaCl (N)[1] | Appearance | Interfacial Tension (dynes) |
| 9 | 0.1 | Cloudy | 0.011 |
| | 0.2 | " | 0.0062 |
| | 0.3 | " | 0.00057 |
| | 0.4 | " | 0.0013 |
| | 0.5 | " | 0.0013 |
| | 0.6 | Two Phases | S.E. |

[1] Normality.
[2] Spontaneous emulsification, the result of a very low interfacial tension.

The above data demonstrates that, in a proper combination with petroleum sulfonates, the A-BIPPE-S of this invention are useful in obtaining low (<0.1 dyne/cm) interfacial tensions in relatively concentrated brine environments. Other combinations of surfactant types and concentrations can be made which also exhibit brine tolerance and low interfacial tensions to an equal or superior degree.

While this invention has been described with specific reference to particular embodiments, it is to be understood that it is not to be limited thereto but is to be construed consistent with the specification and restricted solely by the scope of the appended claims.

What is claimed is:

1. An aqueous anionic surfactant system having a relatively high tolerance to multivalent cations, the system comprising:
   (a) a substantially homogeneous aqueous liquid system containing at least one dissolved or dispersed petroleum sulfonate surfactant in amount which is sufficient to enable the system to displace oil when it is injected into a porous, oil-bearing subterranean rock reservoir; and
   (b) at least one alkylated biphenylyl phenyl ether sulfonate of the formula

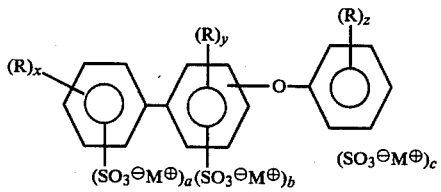

wherein R is an alkyl radical of at least 6 carbon atoms and each R can be the same or different;
$M^{\oplus}$ is hydrogen, alkali metal ion, alkaline earth metal ion or ammonium ion radical and each $M^{\oplus}$ can be the same or different;
a, b and c are individually integers of 0 or 1 with the proviso that the $\Sigma(a+b+c)$ is equal to 2 or 3; and
x, y and z are individually integers of 0-2 with the proviso that $\Sigma(x+y+z) \geq 1$,
said alkylated biphenylyl phenyl ether sulfonate being present in an amount sufficient to improve the multivalent cation tolerance of an aqueous system consisting essentially of water and the petroleum sulfonate surfactant without significantly reducing the interfacial tension-lowering activity of the system.

2. The composition of claim 1 where R is a linear or branched alkyl radical of 8 to about 18 carbon atoms.

3. The composition of claim 2 where $M^{\oplus}$ is an alkali metal ion.

4. The composition of claim 3 where $\Sigma(x+y+z)$ is 1 or 2.

5. The composition of claim 1 where R is a linear or branched alkyl radical of about 10 to about 18 carbon atoms, $M^{\oplus}$ is an ion of sodium or potassium and $\Sigma(x+y+z)$ is 1 or 2.

6. In a process for displacing oil from a porous, subterranean rock reservoir, the process comprising injecting into the reservoir an active aqueous anionic surfactant system, the improvement comprising injecting as said aqueous anionic surfactant system the system of claim 1.

7. An anionic surfactant composition comprising
   (a) a petroleum sulfonate surfactant in an amount which is sufficient to enable an aqueous system containing the composition to displace oil when it is injected into a porous oil-bearing subterranean rock reservoir; and
   (b) at least one alkylated biphenylyl phenyl ether sulfonate of the formula

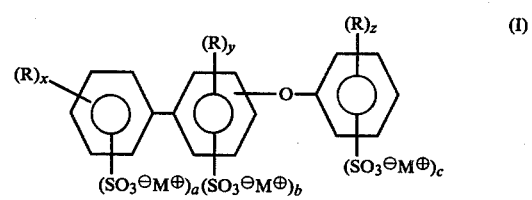

wherein R is an alkyl radical of at least 6 carbon atoms and each R can be the same or different;
$M^{\oplus}$ is hydrogen, alkali metal ion, alkaline earth metal ion or ammonium ion radical and each $M^{\oplus}$ can be the same or different;
a, b and c are individually integers of 0 or 1 with the proviso that the $\Sigma(a+b+c)$ is equal to 2 or 3; and
x, y and z are individually integers of 0-2 with the proviso that $\Sigma(x+y+z) \geq 1$,
said alkylated biphenylyl phenyl ether sulfonate being present in an amount sufficient to improve the multivalent cation tolerance of an aqueous system consisting essentially of water and the petroleum sulfonate surfactant without significantly reducing the interfacial tension-lowering activity of the system.

8. An aqueous anionic surfactant system having a relatively high tolerance to multivalent cations, the system comprising:
   (a) a substantially homogeneous aqueous liquid system containing at least one dissolved or dispersed petroleum sulfonate surfactant in amount which is sufficient to spontaneously emulsify the oil present in a porous subterranean rock reservoir when the system is injected into the reservoir; and
   (b) at least one alkylated biphenylyl phenyl ether sulfonate of the formula

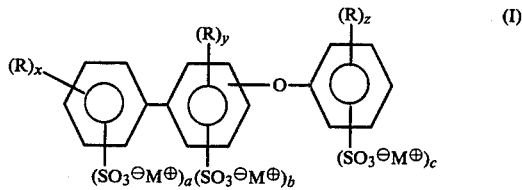

wherein R is an alkyl radical of at least 6 carbon atoms and each R can be the same or different;

$M^{\oplus}$ is hydrogen, alkali metal ion, alkaline earth metal ion or ammonium ion radical and each $M^{\oplus}$ can be the same or different;

a, b and c are individually integers of 0 or 1 with the proviso that the $\Sigma(a+b+c)$ is equal to 2 or 3; and x, y and z are individually integers of 0–2 with the proviso that $\Sigma(x+y+z) \geq 1$, said alkylated biphenylyl phenyl ether sulfonate being present in an amount sufficient to disperse or dissolve the petroleum surfactant in the aqueous system.

* * * * *